United States Patent
Paul et al.

(10) Patent No.: US 12,239,481 B2
(45) Date of Patent: Mar. 4, 2025

(54) ANATOMICAL STRUCTURE IDENTIFICATION APPARATUS AND DISPLAY METHOD THEREOF

(71) Applicant: SAMSUNG MEDISON CO., LTD., Hongcheon-gun Gangwon-do (KR)

(72) Inventors: Anjan Kumar Paul, Seongnam-si (KR); Hojun Lee, Seongnam-si (KR)

(73) Assignee: SAMSUNG MEDISON CO., LTD., Gangwon-do (KR)

( * ) Notice: Subject to any disclaimer, the term of this patent is extended or adjusted under 35 U.S.C. 154(b) by 148 days.

(21) Appl. No.: 17/604,941

(22) PCT Filed: Feb. 12, 2020

(86) PCT No.: PCT/KR2020/001941
§ 371 (c)(1),
(2) Date: Oct. 19, 2021

(87) PCT Pub. No.: WO2020/230984
PCT Pub. Date: Nov. 19, 2020

(65) Prior Publication Data
US 2022/0211340 A1   Jul. 7, 2022

(30) Foreign Application Priority Data
May 15, 2019   (KR) .................. 10-2019-0057132

(51) Int. Cl.
*A61B 8/08*   (2006.01)
*A61B 8/00*   (2006.01)
(52) U.S. Cl.
CPC ............. *A61B 8/08* (2013.01); *A61B 8/463* (2013.01); *A61B 8/469* (2013.01)
(58) Field of Classification Search
CPC ............ A61B 8/08; A61B 8/463; A61B 8/469
See application file for complete search history.

(56) References Cited

U.S. PATENT DOCUMENTS

| | | |
|---|---|---|
| 7,505,805 B2 | 3/2009 | Kuroda |
| 9,865,059 B2 | 1/2018 | Gulaka et al. |

(Continued)

FOREIGN PATENT DOCUMENTS

| | | |
|---|---|---|
| EP | 1757244 A1 | 2/2007 |
| JP | 2007-244746 A | 9/2007 |

(Continued)

OTHER PUBLICATIONS

International Search Report and Written Opinion dated May 25, 2020 issued in International Patent Application No. PCT/KR2020/001941 (with English translation).

(Continued)

*Primary Examiner* — Colin T. Sakamoto
*Assistant Examiner* — Andrew W Begeman
(74) *Attorney, Agent, or Firm* — Morgan, Lewis & Bockius LLP

(57) ABSTRACT

An ultrasonic imaging apparatus and an ultrasonic image display method are disclosed. An ultrasonic imaging apparatus according to one disclosed embodiment can comprise: a display unit; a user interface; a memory for storing one or more instructions; and a processor for executing the one or more instructions so as to determine a reference point in an ultrasonic image, identify at least one anatomical structure of interest on the basis of a location relationship with the reference point with respect to the determined reference point, and control the display unit so that the identified anatomical structure of interest and information about the anatomical structure of interest are displayed.

17 Claims, 10 Drawing Sheets

(56) References Cited

U.S. PATENT DOCUMENTS

| | | | |
|---|---|---|---|
| 10,231,705 B2 | 3/2019 | Lee | |
| 10,426,438 B2 | 10/2019 | Roh et al. | |
| 10,441,249 B2 | 10/2019 | Kim | |
| 10,977,509 B2 | 4/2021 | Feng et al. | |
| 2005/0038423 A1* | 2/2005 | Makin | A61N 7/02 |
| | | | 607/96 |
| 2009/0093717 A1 | 4/2009 | Carneiro et al. | |
| 2010/0249589 A1* | 9/2010 | Lysyansky | A61B 8/466 |
| | | | 600/440 |
| 2011/0237949 A1* | 9/2011 | Zhao | A61B 8/08 |
| | | | 600/443 |
| 2015/0011886 A1 | 1/2015 | Radulescu et al. | |
| 2015/0265251 A1* | 9/2015 | Cho | G06T 7/143 |
| | | | 600/437 |
| 2016/0155222 A1* | 6/2016 | Jeong | G06T 7/11 |
| | | | 382/131 |
| 2016/0183925 A1 | 6/2016 | Kim | |
| 2017/0007161 A1 | 1/2017 | Zou et al. | |
| 2017/0007209 A1* | 1/2017 | Yoo | A61B 8/466 |
| 2017/0181730 A1 | 6/2017 | Ardon et al. | |
| 2018/0296193 A1 | 10/2018 | Cho et al. | |
| 2019/0261949 A1* | 8/2019 | Labyed | G06T 7/0012 |

FOREIGN PATENT DOCUMENTS

| | | |
|---|---|---|
| JP | 2015-500083 A | 1/2015 |
| JP | 2018-175688 A | 11/2018 |
| JP | 6739318 B2 | 8/2020 |
| JP | 6815586 B2 | 1/2021 |
| KR | 10-2015-0089837 A | 8/2015 |
| KR | 10-2015-0108693 A | 9/2015 |
| KR | 10-2015-0108701 A | 9/2015 |
| KR | 10-2016-0051474 A | 5/2016 |
| KR | 10-2016-0081478 A | 7/2016 |
| KR | 10-2018-0065093 A | 6/2018 |
| KR | 10-1876338 B1 | 7/2018 |
| KR | 10-2019-0105301 A | 9/2019 |
| KR | 10-2475822 B1 | 12/2022 |
| WO | 2018/009405 A1 | 1/2018 |

OTHER PUBLICATIONS

G. Lin, et al., "Exploring Context with Deep Structured Models for Semantic Segmentation," IEEE Transaction On Patterns Analysis And Machine Intelligence, vol. 40, No. 6, Jun. 2018, pp. 1352-1366.

T-H Vu, et al., "Context-aware CNNs for person head detection," 2015 IEEE International Conference on Computer, Nov. 24, 2015.

F. I. Alam, et al., "Conditional Random Field and Deep Feature Learning for Hyperspectral Image Classification," IEEE Transactions on Geoscience and Remote Sensing, vol. 57, No. 3, Mar. 2019.

The Extended European Search Report dated May 9, 2023 issued in European Patent Application No. 20805076.5.

Korean Office Action dated Mar. 20, 2024 issued in Korean Patent Application No. 10-2019-0057132 (with English translation).

Notice of Allowance dated Nov. 20, 2024, issued in corresponding Korean Patent Application No. 10-2019-0057132 with an English translation.

* cited by examiner

ANATOMICAL STRUCTURE IDENTIFICATION APPARATUS AND DISPLAY METHOD THEREOF

CROSS-REFERENCE OF RELATED APPLICATIONS

This application is the U.S. National Phase under 35 U.S.C. § 371 of International Patent Application No. PCT/KR2020/001941, filed on Feb. 12, 2020, which in turn claims the benefit of Korean Application No. 10-2019-0057132, filed on May 15, 2019, the entire disclosures of which applications are incorporated by reference herein.

TECHNICAL FIELD

The present invention relates to an ultrasonic imaging apparatus and an ultrasonic image display method. More specifically, the present invention relates to an ultrasonic imaging apparatus for more precisely indentifying an anatomical structure in an ultrasonic image, and a method thereof.

BACKGROUND ART

Ultrasonic imaging apparatuses irradiate an ultrasonic signal generated by a transducer of a probe onto an object and receive information about a signal reflected from the object, thereby acquiring at least one image of an interior part of the object (for example, soft tissue or blood flow). In particular, ultrasonic imaging apparatuses are used for medical purposes for observing the interior of an object, detecting foreign substances, and measuring damage to the object. As compared with X-ray diagnosis apparatuses, such ultrasonic imaging apparatuses have high stability, are able to display images in real time and are safe because there is no radioactive exposure. Therefore, ultrasonic imaging apparatuses are widely used together with other image diagnosis apparatuses including a computed tomography (CT) apparatus, a magnetic resonance imaging (MRI) apparatus, and the like.

DISCLOSURE

Technical Problem

The present invention is directed to providing a method and apparatus for more precisely identifying an anatomical structure in an ultrasonic image.

Technical Solution

According to an embodiment of the present invention, an ultrasonic imaging apparatus includes a display unit, a user interface, a memory configured to store one or more instructions, and a processor configured to execute the one or more instructions to determine a reference point in an ultrasonic image, identify at least one anatomical structure of interest based on a positional relationship with the reference point on the basis of the determined reference point, and control the display unit to display the identified anatomical structure of interest and information about the anatomical structure of interest.

Advantageous Effects

It is possible to determine a reference point in an ultrasonic image, identify at least one anatomical structure of interest based on a positional relationship with the reference point on the basis of the determined reference point, and display the identified anatomical structure of interest and information about the anatomical structure of interest.

DESCRIPTION OF DRAWINGS

The present invention will be understood more fully through the following detailed descriptions taken in conjunction with the accompanying drawings, in which reference numerals denote structural elements.

BEST MODE OF THE INVENTION

Figure 1:
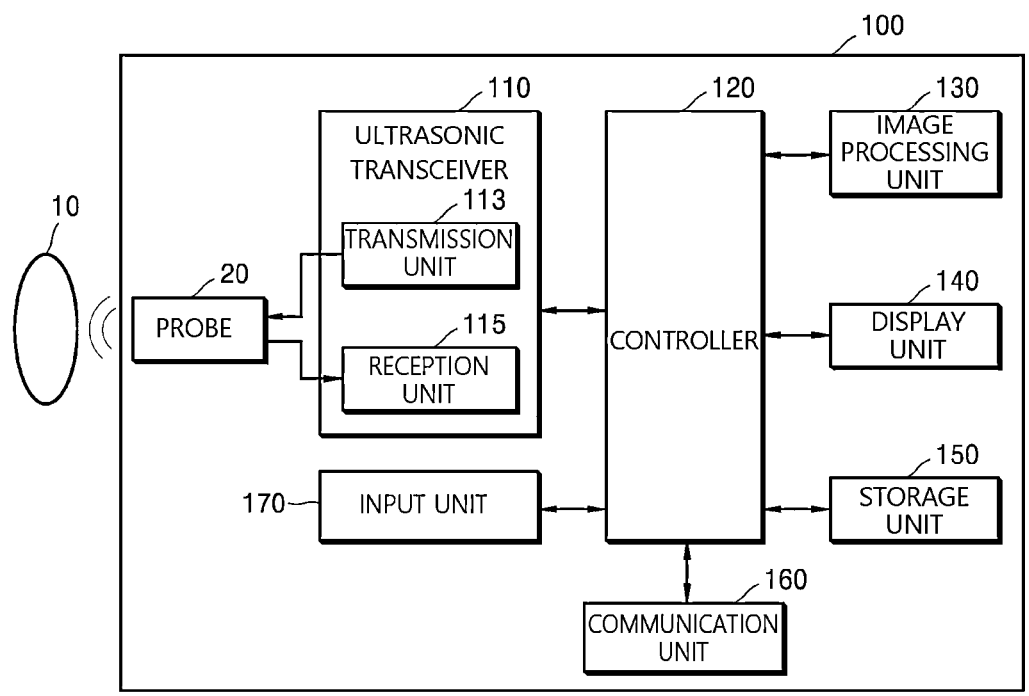
FIG. 1 is a block diagram illustrating a configuration of an ultrasound diagnosis apparatus according to an embodiment.

An ultrasonic imaging apparatus and an ultrasonic image display method are provided.

An ultrasonic imaging apparatus according to an embodiment may include a display unit, a user interface, a memory configured to store one or more instructions, and a processor configured to execute the one or more instructions to determine a reference point in an ultrasonic image, identify at least one anatomical structure of interest based on a positional relationship with the reference point on the basis of the determined reference point, and control the display unit to display the identified anatomical structure of interest and information about the anatomical structure of interest.

[Modes of the Invention]

The present specification describes principles of the present invention and sets forth embodiments thereof to clarify the scope of the present invention and to allow those of ordinary skill in the art to implement the present invention. Disclosed embodiments may be implemented in various forms.

Like reference numerals refer to like elements throughout the specification. The present specification does not describe all elements of embodiments, and common knowledge in the technical field to which the present invention pertains or the same descriptions of the embodiments will be omitted. The term "part" or "portion" used in the specification may be implemented using hardware or software, and according to embodiments, one "part" or "portion" may be implemented as a single unit or element or include a plurality of units or elements. Hereinafter, operating principles and embodiments of the present invention will be described with reference to the accompanying drawings.

In the present specification, an "image" may include a medical image obtained by a medical imaging apparatus such as a magnetic resonance imaging (MRI) device, a computed tomography (CT) device, an ultrasound imaging device, and an X-ray imaging device.

In the present specification, an "object" is to be photographed and may include a person, an animal, or a part thereof. For example, the object may include a part (organ) of a human body, a phantom, or the like.

Throughout the specification, an "ultrasonic image" means an image of the object, which is processed based on an ultrasonic signal transmitted to the object and reflected from the object.

Hereinafter, the embodiments will be described in detail with reference to the accompanying drawings.

FIG. 1 is a block diagram illustrating a configuration of an ultrasound diagnosis apparatus 100 according to an embodiment. The ultrasound diagnosis apparatus 100 may include a probe 20, an ultrasonic transceiver 110, a controller 120, an image processing unit 130, a display unit 140, a storage unit 150, a communication unit 160, and an input unit 170.

The ultrasound diagnosis apparatus 100 may be implemented as a portable type as well as a cart type. Examples of a portable ultrasound diagnosis apparatus may include a smart phone, a laptop computer, a personal digital assistant (PDA), a tablet personal computer (PC), and the like including a probe and an application, but the present invention is not limited thereto.

The probe 20 may include a plurality of transducers. The plurality of transducers may transmit ultrasonic signals to an object 10 according to a transmission signal applied from a transmission unit 113. The plurality of transducers may receive ultrasonic signals reflected from the object 10 to form a reception signal. Further, the probe 20 may be implemented integrally with the ultrasound diagnosis apparatus 100 or may be implemented as a separate type in which the probe 20 is connected to the ultrasound diagnosis apparatus 100 in a wired or wireless manner. Further, the ultrasound diagnosis apparatus 100 may include one or more probes 20 according to an implementation form.

The controller 120 controls the transmission unit 113 to form a transmission signal to be applied to each of the plurality of transducers in consideration of the positions and focal points of the plurality of transducers included in the probe 20.

The controller 120 controls a reception unit 115 to convert a reception signal received from the probe 20 in an analog-to-digital conversion manner and to sum the digitally converted reception signal in consideration of the positions and focal points of the plurality of transducers, thereby generating ultrasonic data.

The image processing unit 130 generates an ultrasonic image using the ultrasonic data generated by the ultrasonic reception unit 115.

The display unit 140 may display the generated ultrasonic image and various pieces of information processed by the ultrasound diagnosis apparatus 100. The ultrasound diagnosis apparatus 100 may include one or more display units 140 according to an implementation form. Further, the display unit 140 may be implemented as a touch screen in combination with a touch panel.

The controller 120 may control the overall operation of the ultrasound diagnosis apparatus 100 and a signal flow between internal components of the ultrasound diagnosis apparatus 100. The controller 120 may include a memory that stores a program or data for performing a function of the ultrasound diagnosis apparatus 100 and a processor that processes the program or data. Further, the controller 120 may control the operation of the ultrasonic diagnosis device 100 by receiving a control signal from the input unit 170 or an external device.

The ultrasound diagnosis apparatus 100 may include the communication unit 160 and may be connected, through the communication unit 160, to an external device (for example, a server, a medical device, a portable device (a smart phone, a tablet PC, a wearable device, and the like)).

The communication unit 160 may include one or more components enabling communication with the external device and may include, for example, at least one of a short-range communication module, a wired communication module, and a wireless communication module.

The communication unit 160 may receive a control signal and data from the external device and transmit the received control signal to the controller 120 so that the controller 120 may control the ultrasound diagnosis apparatus 100 in response to the received control signal.

Alternatively, the controller 120 may transmit a control signal to the external device through the communication unit 160 so that the external device may be controlled in response to the control signal of the controller 120.

For example, the external device may process the data of the external device in response to the control signal of the controller received through the communication unit.

A program capable of controlling the ultrasound diagnosis apparatus 100 may be installed in the external device, and the program may include instructions for performing some or all of the operations of the controller 120.

The program may be installed in the external device in advance or may be installed by a user of the external device by downloading the program from a server that provides applications. The server that provides applications may include a recording medium in which the corresponding program is stored.

The storage unit 150 may store various types of data or programs for driving and controlling the ultrasound diagnosis apparatus 100, input/output ultrasonic data, acquired ultrasonic images, and the like.

The input unit 170 may receive a user's input to control the ultrasound diagnosis device 100. For example, the user's input may include an input for manipulating a button, a keypad, a mouse, a trackball, a jog switch, a knob, or the like, an input for touching a touchpad or a touch screen, a voice input, a motion input, and a bioinformation input (e.g., iris recognition or fingerprint recognition), but the present disclosure is not limited thereto.

An example of the ultrasound diagnosis device 100 according to an embodiment will be described below with reference to FIGS. 2A to 2C.

Figure 2C:
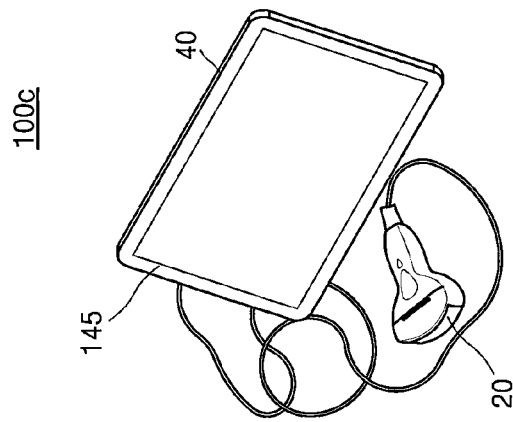
FIGS. 2A to 2C are views illustrating ultrasound diagnosis apparatuses according to an embodiment.
Figure 2B:
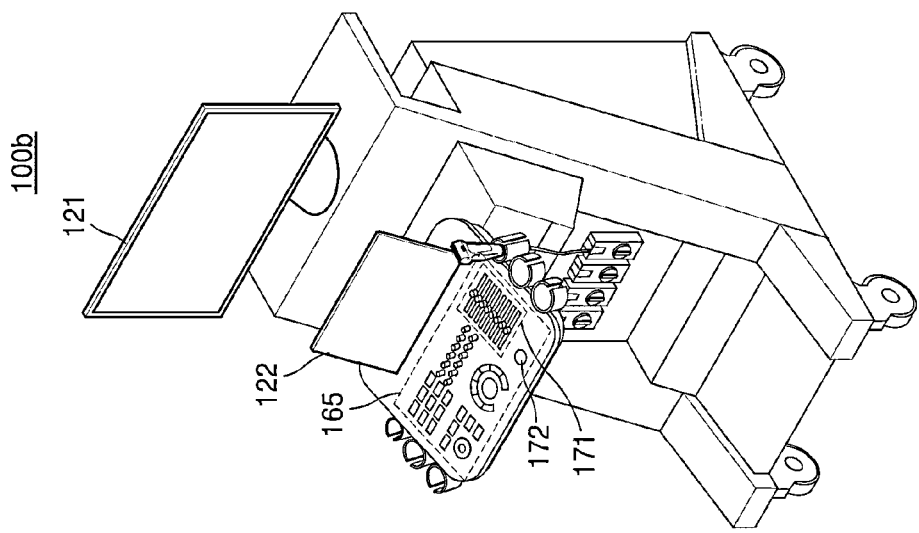
Figure 2A:
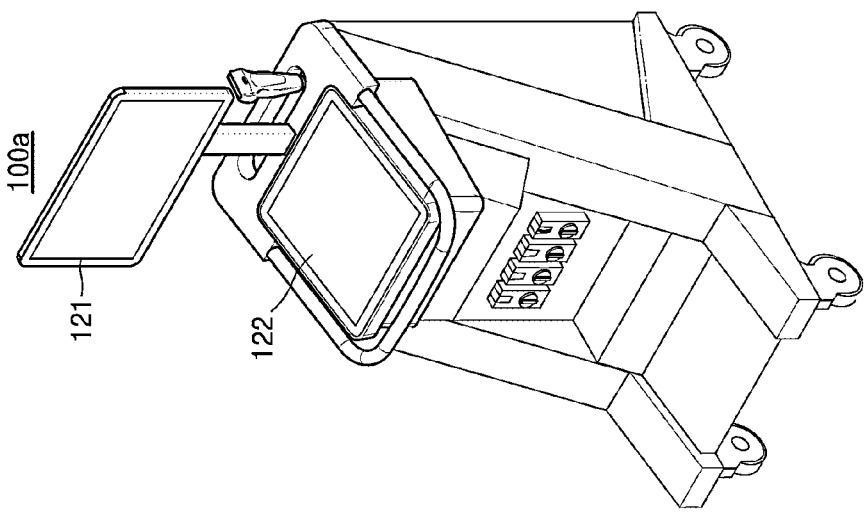

FIGS. 2A to 2C are views illustrating ultrasound diagnosis apparatuses according to an embodiment.

Referring to FIGS. 2A and 2B, ultrasound diagnosis apparatuses 100a and 100b may each include a main display unit 121 and a sub display unit 122. One of the main display unit 121 and the sub display unit 122 may be implemented as a touch screen. The main display unit 121 and the sub display unit 122 may display the ultrasonic image or various pieces of information processed by the ultrasound diagnosis apparatuses 100a and 100b. Further, the main display unit 121 and the sub display unit 122 may be implemented as a touch screen and provide a graphical user interface (GUI) to receive data for controlling the ultrasound diagnosis apparatuses 100a and 100b from a user. For example, the main display unit 121 may display the ultrasonic image, and the sub display unit 122 may display a control panel for controlling the ultrasonic image in the form of the GUI. The sub display unit 122 may receive data for controlling the displaying of the image through the control panel displayed in the form of the GUI. The ultrasound diagnosis apparatuses 100a and 100b may control, using input control data, the displaying of the ultrasonic image displayed on the main display unit 121.

Referring to FIG. 2B, the ultrasound diagnosis apparatus 100b may further include a control panel 165 in addition to the main display unit 121 and the sub display unit 122. The control panel 165 may include a button, a trackball, a jog switch, a knob, and the like, and may receive data for controlling the ultrasound diagnosis apparatus 100b from the user. For example, the control panel 165 may include a time gain compensation (TGC) button 171, a freeze button 172, and the like. The TGC button 171 is a button for setting a TGC value for each depth of the ultrasonic image. Further, when detecting the input of the freeze button 172 while scanning the ultrasonic image, the ultrasound diagnosis apparatus 100b may maintain a state in which a frame image at a corresponding time point is displayed.

Meanwhile, inputs of the button, the trackball, the jog switch, the knob, and the like included in the control panel 165 may be provided to the GUI in the main display unit 121 or the sub display unit 122.

Referring to FIG. 2C, the ultrasound diagnosis apparatus 100c may be implemented as a portable type.

Examples of a portable ultrasound diagnosis apparatus 100c may include a smart phone, a laptop computer, a PDA, a tablet PC, and the like including a probe and an application, but the present invention is not limited thereto.

The ultrasound diagnosis apparatus 100c may include the probe 20 and a main body 40, and the probe 20 may be connected to one side of the main body 40 in a wired or wireless manner. The main body 40 may include a touch screen 145. The touch screen 145 may display the ultrasonic image, various pieces of information processed by the ultrasound diagnosis apparatus, the GUI, and the like.

Figure 3:
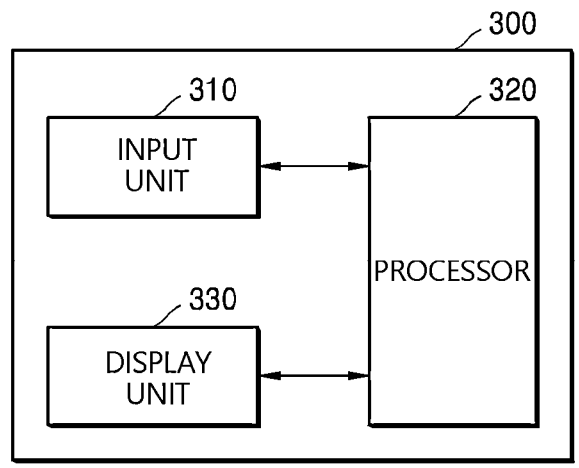
FIG. 3 is a block diagram illustrating a configuration of an ultrasonic imaging apparatus according to an embodiment.

FIG. 3 is a block diagram illustrating a configuration of an ultrasonic imaging apparatus according to an embodiment.

An ultrasonic imaging apparatus 300 according to the embodiment includes an input unit 310, a processor 320, and a display unit 330. The ultrasonic imaging apparatus 300 may correspond to the ultrasonic imaging device 100 of FIG. 1. In addition, the ultrasonic imaging apparatus 300 may be implemented as a type of one of the ultrasonic imaging devices 100A, 100b, and 100C illustrated in FIG. 2. In an embodiment, the input unit 310 of FIG. 3 may include the input unit 170 of FIG. 1. In addition, the processor 320 may correspond to the controller 120 and the image processing unit 130 of FIG. 1. The processor 320 may include one or more processors. The display unit 330 may correspond to the display unit 140 of FIG. 1.

According to an embodiment, the ultrasonic imaging apparatus 300 may include fewer components than those shown in FIG. 3 or further include other additional components. For example, the ultrasonic imaging apparatus 300 may receive a user input from a separate device instead of including the input unit 310.

The input unit 310 according to the embodiment may acquire ultrasonic data about an object. For example, the input unit 310 may use a probe 20 to irradiate ultrasonic waves onto the object and detect an ultrasonic echo signal. In an embodiment, the object may be a part of a user's body including a wrist.

In an embodiment, the probe may be a freehand type probe. In addition, the probe may be a linear probe or a 2-dimensional matrix array type probe, but in the present embodiment, the type of the probe is not limited to the above-described examples.

The processor 320 controls the overall operation of the ultrasonic imaging apparatus 300 and processes data and signals. The processor 320 may include at least one hardware unit. According to an embodiment, the processor 320 may include separate hardware units serving as an image processing unit and a controller. The processor 320 may be operated by one or more software modules generated by executing program codes stored in a memory.

The processor 320 may acquire ultrasonic image data about an object from an ultrasonic echo signal. The processor 320 may acquire ultrasonic image data including at least one of brightness mode (B-mode) image data, spectral Doppler image data, color Doppler image data, elastic image data, and motion mode (M mode) image data from the ultrasonic echo signal, but the type of the ultrasonic image data acquirable by the processor 320 is not limited thereto.

In an embodiment, the ultrasonic image data may be object section data. The object section data may include a certain piece of volume data acquired based on a 2-dimensional section of the object or consecutive 2-dimensional sections. That is, for example, the object section data may be 2-dimensional image data showing a cross section of an object or 3-dimensional image data about a certain volume including a plurality of cross sections of the object.

The processor 320 may determine a reference point in ultrasonic image data.

In an embodiment, the reference point may be a specific position in an ultrasonic image. In an embodiment, the above-described reference point may be determined based on an input of a user. For example, the reference point may be determined based on a click event of the user at a specific position or an input of the user related to position coordinates. However, a method in which the user inputs information related to the reference point is not limited to the above-described embodiment. In another embodiment, the above-described reference point may be determined based on a predetermined certain criterion. For example, the reference point may be an absolute position in an ultrasonic image, for example, a position of center coordinates. Alternatively, the reference point may be a certain position in a determined region of interest on an ultrasonic image, for example, a position of center coordinates in the region of interest. However, the certain criterion is not limited to the above-described embodiment.

In an embodiment, the reference point may be a point at which a reference anatomical structure is located on an ultrasonic image or may be a central position of the reference anatomical structure. In an embodiment, the reference anatomical structure may be determined based on an input of a user. For example, the reference anatomical structure may be determined based on an input of the user of selecting a specific anatomical structure from among a plurality of anatomical structures. In an embodiment, the ultrasonic imaging apparatus 300 may display information indicating a plurality of anatomical structures, for example, an icon corresponding to each anatomical structure or text representing a name thereof, through the display unit 330 and may receive an input of the user of selecting at least one anatomical structure from among the plurality of anatomical structures described above. Alternatively, the ultrasonic imaging apparatus 300 may receive a text input representing a name of an anatomical structure from the user and may select the anatomical structure corresponding to the above-described text input as the reference anatomical structure using a database stored in a memory or received from an external device. However, a method in which the user inputs information about the reference anatomical structure is not limited to the above-described embodiment.

In another embodiment, the reference anatomical structure may be at least one predetermined anatomical structure. Information about at least one predetermined anatomical structure may be stored in a memory of the ultrasound diagnosis apparatus 300. When the ultrasound diagnosis apparatus 300 performs an ultrasonic image displaying operation, the ultrasound diagnosis apparatus 300 may automatically select the above-described at least one predetermined anatomical structure as the reference anatomical structure. In an embodiment, the reference anatomical structure may be an anatomical structure that is easy to identify on an ultrasonic image. For example, when an object is a wrist of a user, the reference anatomical structure may be an ulnar nerve or a flexor pollicis longus tendon of the user. However, it will be understood by a person skilled in the art that the reference anatomical structure is not limited to the above-described embodiment.

On the basis of the determined reference point, the processor 320 may identify at least one anatomical structure of interest in the ultrasonic image based on a relationship between the anatomical structure of interest and the above-described reference point, for example, a positional relationship therebetween.

The anatomical structure of interest may be an anatomical structure to be identified in the ultrasonic image. In an embodiment, the anatomical structure of interest may be determined based on an input of a user or may be a predetermined anatomical structure.

In an embodiment, the anatomical structure of interest may be determined based on an input of the user of selecting a specific anatomical structure from among a plurality of anatomical structures. In an embodiment, the ultrasonic imaging apparatus 300 may display information indicating a plurality of anatomical structures, for example, an icon corresponding to each anatomical structure or text representing a name thereof, through the display unit 330 and may receive an input of the user of selecting at least one anatomical structure from among the plurality of anatomical structures described above. Alternatively, the ultrasonic imaging apparatus 300 may receive a text input representing a name of an anatomical structure from the user and may select the anatomical structure corresponding to the above-described text input as the reference anatomical structure using a database stored in the memory or received from the external device. However, a method in which the user inputs information about the anatomical structure of interest is not limited to the above-described embodiment.

In another embodiment, the anatomical structure of interest may be at least one predetermined anatomical structure. In an embodiment, the anatomical structure of interest may be a diagnostically important anatomical structure. For example, when an object is a wrist of a user, the reference anatomical structure may be an ulnar nerve or a median nerve of the user. However, it will be understood by a person skilled in the art that the reference anatomical structure is not limited to the above-described embodiment.

The positional relationship between the anatomical structure of interest and the reference point may include various types of information. For example, the positional relationship may include at least one of a 2-dimensional or 3-dimensional distance value, a direction, and a natural language description indicating such information between the anatomical structure of interest and the reference point.

Meanwhile, when the processor 320 cannot identify at least one anatomical structure of interest, on the basis of the determined reference point, the processor 320 may acquire an estimated position of at least one anatomical structure of interest on the ultrasonic image based on the positional relationship between the anatomical structure of interest and the above-described reference point. In addition, the processor 320 may calculate the probability of the acquired estimated position of the anatomical structure of interest.

In an embodiment, the processor 320 may identify at least one anatomical structure of interest or the estimated position of the anatomical structure of interest on the ultrasonic image based on a learning model (or a learning network model). More specifically, the processor 320 may identify the anatomical structure of interest or acquire the estimated position thereof on the ultrasonic image by applying data about the reference point and the anatomical structure of interest to the learning model.

In an embodiment, in order to train the above-described learning model, position context information may be provided to the learning model. The position context information may include at least one of a 2-dimensional or 3-dimensional distance value, a direction, and a natural language description indicating such information between anatomical structures, but the present invention is not limited thereto.

The processor 320 may control the display unit 330 to display the identified at least one anatomical structure of interest and information about the anatomical structure of interest.

The display unit 330 displays an operation state of the ultrasonic imaging apparatus 300, an ultrasonic image, a user interface screen, and the like. The display unit 330 may include one or more display panels according to embodiments. According to an embodiment, the display unit 330 may be implemented in the form of a touch screen.

The display unit 330 according to the embodiment may display the identified at least one anatomical structure of interest and the information about the anatomical structure of interest. In an embodiment, the at least one anatomical structure of interest and the information about the anatomical structure of interest may be displayed on an ultrasonic image or displayed parallel with the ultrasonic image.

In an embodiment, the anatomical structure of interest may be displayed in the form of a closed curve on the ultrasonic image. The above-described closed curve may be displayed along a contour line of the anatomical structure of interest. In another embodiment, the anatomical structure of interest may be displayed in the form of a specific face on the ultrasonic image. The above-described face may represent a cross section of the anatomical structure of interest. For example, the above-described face may be filled with a certain type of color or may be filled with a certain type of geometric pattern, for example, a hatched pattern. In another embodiment, the anatomical structure of interest may be displayed on the ultrasonic image in the form of a specific identifier, for example, a dot, a box, or an arrow. The above-described specific identifier may be displayed at a central position of the anatomical structure of interest. In still another embodiment, the anatomical structure of interest may be displayed on the ultrasonic image in the form of an icon corresponding to the anatomical structure of interest or text representing a name thereof. The icon or text representing the name may be displayed at a position which does not overlap the cross section of the anatomical structure of interest and is adjacent to the cross section of the anatomical structure of interest.

In an embodiment, the information about the anatomical structure of interest may be information indicating the positional relationship between the anatomical structure of interest and the reference point. In an embodiment, the above-described positional relationship may be displayed in the form of a distance map. The distance map may include at least one of information indicating a distance between the anatomical structure of interest and the reference point and a line connecting the anatomical structure of interest and the reference point. In an embodiment, the above-described positional relationship may be displayed in the form of a distance table. The distance table may include information in which a distance between at least one anatomical structure of interest and the reference point is displayed in the form of a table. In an embodiment, the above-described positional relationship may be displayed in the form of a distance color map. The distance color map may include information in which a distance between at least one anatomical structure of interest and the reference point is displayed in the form of a color. In an embodiment, the above-described positional relationship may be displayed in the form of a natural language description. For example, when the reference point is a position of an ulnar nerve and the anatomical structure of interest is a median nerve, the above-described positional relationship may be displayed in the form of a natural language description of "median nerve located on left side of ulnar nerve."

Meanwhile, when the estimated position of the anatomical structure of interest is acquired, the processor 320 may control the display unit 330 to display the above-described estimated position and the information about the anatomical structure of interest. In addition, the processor 320 may control the display unit 330 to further display the probability of the estimated position of the anatomical structure of interest.

In an embodiment, the estimated position of the anatomical structure of interest may be displayed in the form of a closed curve on the ultrasonic image. The above-described closed curve may be displayed along an estimated contour line of the anatomical structure of interest. In another embodiment, the anatomical structure of interest may be displayed in the form of a specific face on the ultrasonic image. The above-described face may represent an estimated cross section of the anatomical structure of interest. For example, the above-described face may be filled with a certain type of color or may be filled with a certain type of geometric pattern, for example, a hatched pattern. In another embodiment, the estimated position of the anatomical structure of interest may be displayed on the ultrasonic image in the form of a specific identifier, for example, a box, a dot, or an arrow. The above-described specific identifier may be displayed at a central position of the anatomical structure of interest. In still another embodiment, the estimated position of the anatomical structure of interest may be displayed on the ultrasonic image in the form of an icon corresponding to the anatomical structure of interest or text representing a name thereof. The above-described icon or text representing the name may be displayed at a position which does not overlap the cross section of the anatomical structure of interest and is adjacent to the cross section of the anatomical structure of interest.

In an embodiment, the probability of the estimated position may be displayed in the form of text representing a reliability value. For example, the reliability value may be a percentage value that indicates a probability or a probability value that is less than one.

In an embodiment, the probability of the estimated position may be displayed in the form of at least one of a color or type of an identifier, a color or geometric pattern type of a face, and a thickness or type of a line which indicate the estimated position on the ultrasonic image. For example, when the estimated position is displayed in the form of a box, a line thickness of the box indicating the estimated position may be decreased as a probability is lowered. Alternatively, when the estimated position is displayed in the form of a closed curve, the closed curve indicating the estimated position may be displayed as a dotted line when a probability is less than or equal to a certain probability. However, a method of displaying a probability in the present invention is not limited to the above-described embodiment.

Meanwhile, according to embodiments, the ultrasound diagnosis apparatus 300 may further include the memory in addition to the processor 320 and the display unit 330. The above-described learning network model may be stored in the memory of the ultrasound diagnosis apparatus 300.

The learning network model may be designed to simulate a human brain structure on a computer.

For example, the learning network model may include a plurality of network nodes that simulate neurons of a human neural network and have a weight. The plurality of network nodes may each establish a connection relation so that the neurons simulate synaptic activity of transmitting and receiving signals through synapses.

The learning network model may include, for example, an artificial intelligence neural network model or a deep learning network model developed from a neural network model. In the deep learning network model, a plurality of network nodes may be located at different depths (or layers) and may exchange data according to a convolution connection relationship.

As an example, the learning network model may be implemented as a software module. When being implemented as the software module (for example, a program module including instructions), the learning network model may be stored in a computer-readable medium. In this case, the computer-readable recording medium may become at least a part of a memory 1500.

As another example, the learning network model may be integrated in the form of a hardware chip and become a part of the processor 320. For example, the learning network model may be manufactured in the form of a dedicated hardware chip for artificial intelligence (AI) or may be manufactured as a part of an existing general-purpose processor (for example, a central processing unit (CPU) or an application processor) or a dedicated graphic processor (for example, a graphic processing unit (GPU)).

Alternatively, the learning network model may be stored in an external server. In this case, the ultrasound diagnosis apparatus 300 may use the above-described learning network model while transmitting and receiving data to and from the external server.

In this case, the ultrasound diagnosis apparatus 300 may transmit an ultrasonic image to the above-described external server through a communication unit. For example, the external server may be an AI cloud server. The ultrasonic image may be, for example, an image acquired by a sonographer operating the ultrasound diagnosis apparatus 300 according to a protocol.

The external server may input the ultrasonic image received from the ultrasound diagnosis apparatus 300 to the learning network model to analyze the ultrasonic image and may transmit information about a relative position of a target anatomical structure and a determined target anatomical structure to the ultrasound diagnosis apparatus 300.

When the learning network model located in the external server is implemented as a software module, the learning network model may be stored in a computer-readable recording medium. In this case, the computer-readable recording medium may become a memory (not shown) of the server.

The learning network model may be created in the external server. The external server may be, for example, a server of a manufacturer of the ultrasound diagnosis apparatus 300, a server of a manager, or a server of a third party consigned or leased by the manufacturer or manager. The server may be a server which only creates or updates a learning network model or may be a server which receives an ultrasonic image from the ultrasound diagnosis apparatus 300 and provides an analysis result using the learning network model.

The server may train the training network model using training data. The training data may be, for example, information indicating a positional relationship between various anatomical structures. The positional relationship may include at least one of natural language descriptions indicating a distance value, a direction, and the positional relationship between the anatomical structures. Medical image information may include an ultrasonic image, an X-ray image, an MRI image, and a CT image.

The training data may be collected from a hospital or a doctor by the manufacturer or manager of the ultrasound diagnosis apparatus 300, or a result obtained using the learning network model in the ultrasound diagnosis apparatus 300 may be used again as the training data.

The learning network model may be updated periodically or aperiodically. The aperiodic updating may be performed, for example, when there is a request from the manager or when more than a certain amount of the training data is collected.

According to various embodiments, a process of generating the learning network model may be directly performed by the ultrasound diagnosis apparatus 300. That is, the ultrasound diagnosis apparatus 300 may train and update the learning network model and even analyze an ultrasonic image using the learning network model.

In addition, the server may be provided as a plurality of servers. The server may include a system which stores and processes data using resources of various devices (servers, clients, or the like) connected to each other in the Internet environment.

According to embodiments of the present invention, the learning network model may be configured to estimate the optimal positional relationship and a position of an anatomical structure with respect thereto.

Here, the learning network model being configured for the above purpose means that the learning network model is not a general learning network model capable of responding to various cases but is a learning network model which is trained for a specific purpose and thus the inside thereof is implemented to meet the above purpose.

Figure 4:
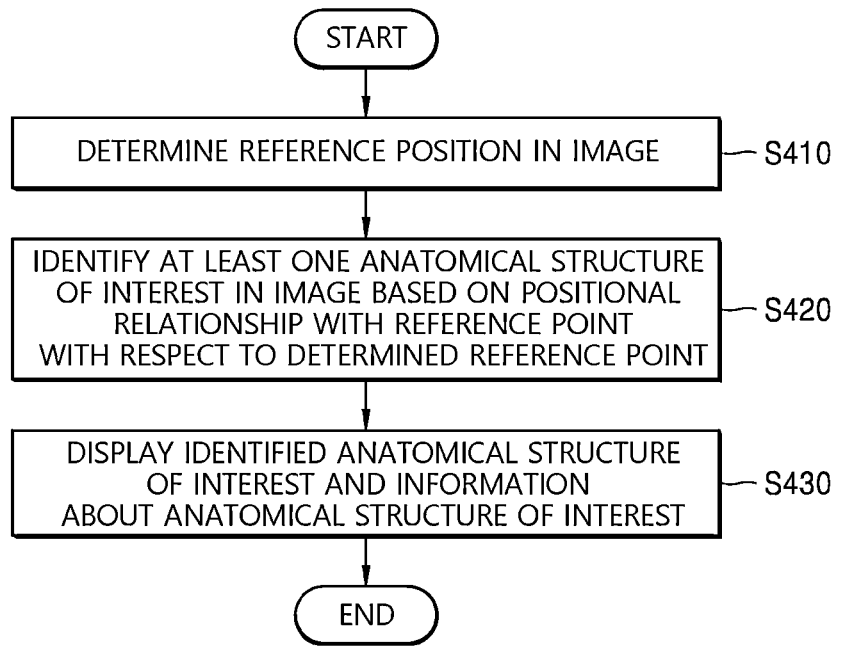
FIG. 4 is a flowchart illustrating an ultrasonic image display method according to an embodiment.

FIG. 4 is a flowchart illustrating an ultrasonic image display method according to an embodiment.

In operation S410, a reference point may be determined in an ultrasonic image.

In an embodiment, the above-described reference point may be determined based on an input of a user or based on a predetermined certain criterion. In another embodiment, the reference point may be a point at which a reference anatomical structure is located on the ultrasonic image, or a central position of the reference anatomical structure. In an embodiment, the reference anatomical structure may be determined based on an input of the user or may be at least one predetermined anatomical structure. In an embodiment, the reference anatomical structure may be an anatomical structure that is easy to identify on the ultrasonic image. For example, when an object is a wrist of the user, the reference anatomical structure may be an ulnar nerve or a flexor pollicis longus tendon of the user. However, it will be understood by a person skilled in the art that the reference anatomical structure is not limited to the above-described embodiment.

In operation S420, on the basis of the determined reference point, at least one anatomical structure of interest may be identified based on a positional relationship with the above-described reference point.

The anatomical structure of interest may be an anatomical structure to be identified in the ultrasonic image. In an embodiment, the anatomical structure of interest may be determined based on an input of the user or may be a predetermined anatomical structure.

The positional relationship between the anatomical structure of interest and the reference point may include various types of information. For example, the positional relationship may include at least one of a 2-dimensional or 3-dimensional distance value, a direction, and a natural language description indicating such information between the anatomical structure of interest and the reference point.

In an embodiment, an ultrasound diagnosis apparatus may identify at least one anatomical structure of interest on the ultrasonic image based on a learning model (or a learning network model). More specifically, the ultrasound diagnosis apparatus may identify the anatomical structure of interest on the ultrasonic image by applying data about the reference point and the anatomical structure of interest to the learning model.

In operation S430, the identified anatomical structure of interest and information about the anatomical structure of interest may be displayed. In an embodiment, at least one anatomical structure of interest and the information about the anatomical structure of interest may be displayed on the ultrasonic image or displayed parallel with the ultrasonic image.

In an embodiment, the anatomical structure of interest may be displayed on the ultrasonic image in the form of at least one of a closed curve, a face indicating a cross section of the anatomical structure of interest, a specific identifier, an icon corresponding to the anatomical structure of interest, and text representing a name of the anatomical structure of interest. However, a method of displaying the anatomical structure of interest on the ultrasonic image is not limited to the above-described example.

In an embodiment, the information about the anatomical structure of interest may be information indicating the positional relationship between the anatomical structure of interest and the reference point. In an embodiment, the above-described positional relationship may be displayed in the form of a distance map. The distance map may include at least one of information indicating a distance between the anatomical structure of interest and the reference point and a line connecting the anatomical structure of interest and the reference point. In an embodiment, the above-described positional relationship may be displayed in the form of a distance table. The distance table may include information in which a distance between at least one anatomical structure of interest and the reference point is displayed in the form of a table. In an embodiment, the above-described positional relationship may be displayed in the form of a distance color map. The distance color map may include information in which a distance between at least one anatomical structure of interest and the reference point is displayed in the form of a color. In an embodiment, the above-described positional relationship may be displayed in the form of a natural language description. For example, when the reference point is a position of an ulnar nerve, and the anatomical structure of interest is a median nerve, the above-described positional relationship may be displayed in the form of a natural language description of "median nerve located on left side of ulnar nerve."

According to the ultrasonic image display method described with reference to FIG. 4, the ultrasound diagnosis apparatus identifies the anatomical structure of interest based on the positional relationship between the reference point and the anatomical structure of interest and displays the identified anatomical structure and information thereabout, thereby providing more various pieces of information to a user and allowing the anatomical structure of interest to be more easily analyzed.

Figure 5:
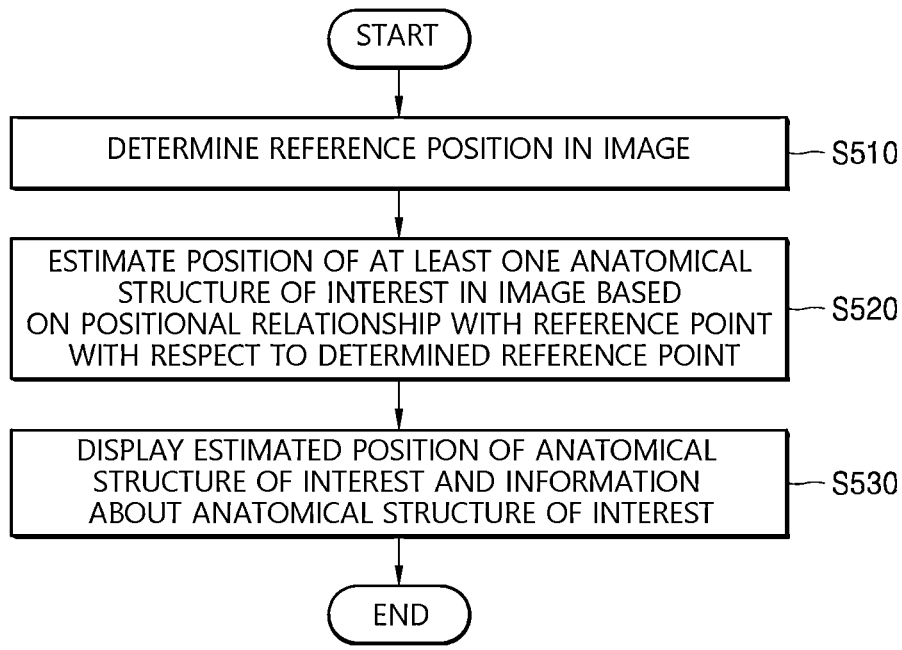
FIG. 5 is a flowchart illustrating an ultrasonic image display method according to an embodiment.

FIG. 5 is a flowchart illustrating an ultrasonic image display method according to an embodiment.

In operation S510, a reference point may be determined in an ultrasonic image.

In an embodiment, the above-described reference point may be determined based on an input of a user or based on a predetermined certain criterion. In another embodiment, the reference point may be a point at which a reference anatomical structure is located on the ultrasonic image, or a central position of the reference anatomical structure. In an embodiment, the reference anatomical structure may be determined based on an input of the user or may be at least one predetermined anatomical structure. In an embodiment, the reference anatomical structure may be an anatomical structure that is easy to identify on the ultrasonic image. For example, when an object is a wrist of a user, the reference anatomical structure may be an ulnar nerve or a flexor pollicis longus tendon of the user. However, it will be understood by a person skilled in the art that the reference anatomical structure is not limited to the above-described embodiment.

In operation S520, on the basis of the determined reference point, an estimated position of at least one anatomical structure of interest may be acquired based on a positional relationship with the above-described reference point. In an embodiment, the estimated position of the anatomical structure of interest may be acquired when at least one anatomical structure of interest cannot be identified in the embodiment described with reference to FIG. 4. In addition, the probability of the acquired estimated position of the anatomical structure of interest may be calculated.

The anatomical structure of interest may be an anatomical structure to be identified in the ultrasonic image. In an embodiment, the anatomical structure of interest may be determined based on an input of the user or may be a predetermined anatomical structure.

The positional relationship between the anatomical structure of interest and the reference point may include various types of information. For example, the positional relationship may include at least one of a 2-dimensional or 3-dimensional distance value, a direction, and a natural language description indicating such information between the anatomical structure of interest and the reference point.

In an embodiment, an ultrasound diagnosis apparatus may acquire the estimated position of at least one anatomical structure of interest on the ultrasonic image based on a learning model (or a learning network model). More specifically, the ultrasound diagnosis apparatus may acquire the estimated position of the anatomical structure of interest on the ultrasonic image by applying data about the reference point and the anatomical structure of interest to the learning model.

In operation S530, the estimated position of the anatomical structure of interest and information about the anatomical structure of interest may be displayed. In an embodiment, the estimated position of the at least one anatomical structure of interest and the information about the anatomical structure of interest may be displayed on the ultrasonic image or displayed parallel with the ultrasonic image. In addition, in an embodiment, the probability of the estimated position may be further displayed.

In an embodiment, the estimated position of the anatomical structure of interest may be displayed on the ultrasonic image in the form of at least one of a closed curve, a face indicating a cross section of the anatomical structure of interest, a specific identifier, an icon corresponding to the anatomical structure of interest, and text representing a name of the anatomical structure of interest. However, a method of displaying the estimated position of the anatomical structure of interest on the ultrasonic image is not limited to the above-described example.

In an embodiment, the information about the anatomical structure of interest may be information indicating the positional relationship between the anatomical structure of interest and the reference point. In an embodiment, the above-described positional relationship may be displayed in the form of a distance map. The distance map may include at least one of information indicating a distance between the anatomical structure of interest and the reference point and a line connecting the anatomical structure of interest and the reference point. In an embodiment, the above-described positional relationship may be displayed in the form of a distance table. The distance table may include information in which a distance between at least one anatomical structure of interest and the reference point is displayed in the form of a table. In an embodiment, the above-described positional relationship may be displayed in the form of a distance color map. The distance color map may include information in which a distance between at least one anatomical structure of interest and the reference point is displayed in the form of a color. In an embodiment, the above-described positional relationship may be displayed in the form of a natural language description. For example, when the reference point is a position of an ulnar nerve, and the anatomical structure of interest is a median nerve, the above-described positional relationship may be displayed in the form of a natural language description of "median nerve located on left side of ulnar nerve."

In an embodiment, the probability of the estimated position may be displayed in the form of text representing a reliability value. For example, the reliability value may be a percentage value that indicates a probability or a probability value that is less than 1. For example, when the reference point is a position of an ulnar nerve, and the anatomical structure of interest is a median nerve, the above-described positional relationship may be displayed in the form of a natural language description of "median nerve located on left side of ulnar nerve, probability 0.88."

In an embodiment, the probability of the estimated position may be displayed in the form of at least one of a color or type of an identifier, a color or geometric pattern type of a face, and a thickness or type of a line which indicate the estimated position on the ultrasonic image. For example, when the estimated position is displayed in the form of a box, a line thickness of the box indicating the estimated position may be decreased as a probability is lowered. Alternatively, when the estimated position is displayed in the form of a closed curve, the closed curve indicating the estimated position may be displayed as a dotted line when a probability is less than or equal to a certain probability. However, a method of displaying a probability in the present disclosure is not limited to the above-described embodiment.

According to the ultrasonic image display method described with reference to FIG. 5, the ultrasound diagnosis apparatus estimates the anatomical structure of interest based on the positional relationship between the reference point and the anatomical structure of interest and displays the estimated position and information thereabout, thereby allowing a user to more easily analyze the anatomical structure of interest even when the anatomical structure is difficult to identify.

Figure 6A:
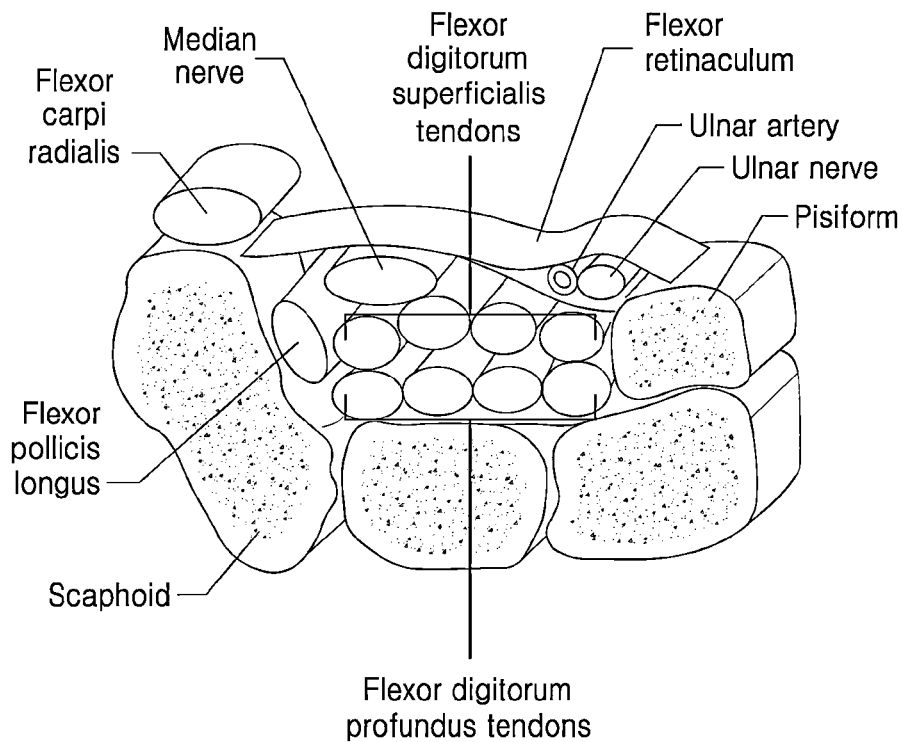
FIG. 6A is a view for describing a proximal carpal tunnel.
Figure 6B:
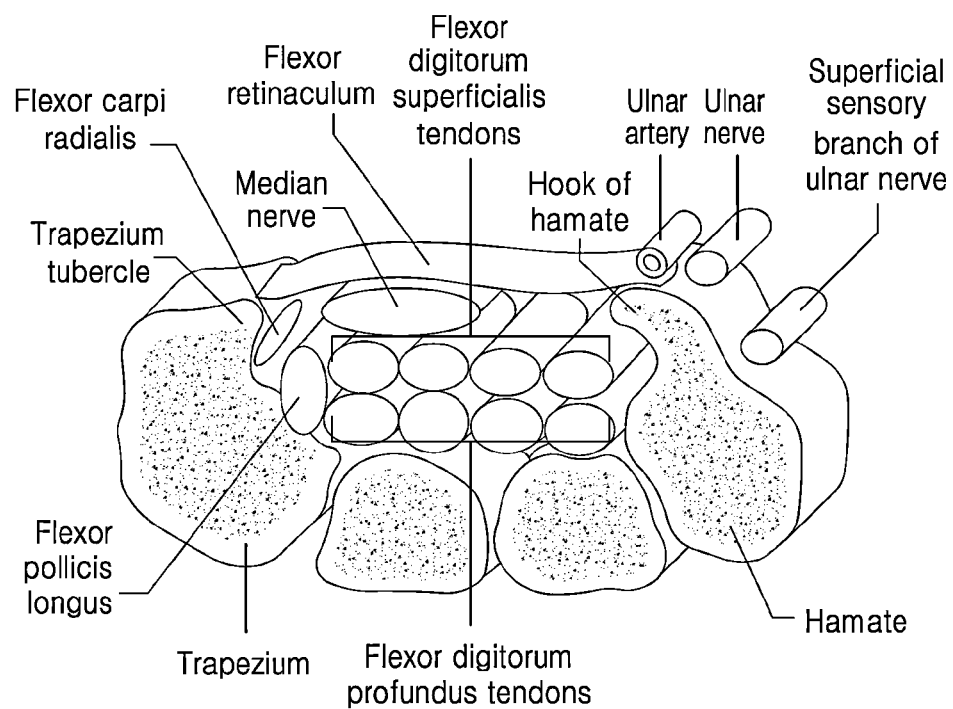
FIG. 6B is a view for describing a distal carpal tunnel.

FIGS. 6A and 6B are views for describing an anatomical structure of a carpal tunnel.

FIG. 6A is a view for describing a proximal carpal tunnel. Referring to FIG. 6A, FIG. 6A illustrates landmark anatomical structures of the proximal carpal tunnel, such as an ulnar artery, an ulnar nerve, a median nerve, a scaphoid tubercle, a pisiform, a flexor retinaculum, and a flexor pollicis longus. When an ultrasonic image including the proximal carpal tunnel is acquired, at least one of the landmark anatomical structures may be selected as a reference anatomical structure or an anatomical structure of interest. For example, the scaphoid tubercle or the pisiform, which is a bony landmark that is easy to identify, may be selected as the reference anatomical structure. In addition, in order to avoid conflict when a tunnel syndrome is diagnosed or a drug is injected, the identification of a nervous structure may be required, and thus, the ulnar nerve or the median nerve, which is a major nerve landmark, may be selected as the anatomical structure of interest. However, this is merely an example, and a method of selecting the reference anatomical structure or the anatomical structure of interest is not limited to the above-described embodiment.

FIG. 6B is a view for describing a distal carpal tunnel. Referring to FIG. 6B, Landmark anatomical structures of the distal carpal tunnel, such as an ulnar artery, an ulnar nerve, a median nerve, a trapezium tubercle, a hook of hamate, a flexor retinaculum, and a flexor pollicis longus are illustrated. When an ultrasonic image including the distal carpal tunnel is acquired, at least one of the landmark anatomical structures may be selected as a reference anatomical structure or an anatomical structure of interest. For example, the trapezium tubercle or the hook of hamate, which is a bony landmark that is easy to identify, may be selected as the reference anatomical structure. In addition, in order to avoid conflict when a tunnel syndrome is diagnosed or a drug is injected, the identification of a nervous structure may be required, and thus, the ulnar nerve or the median nerve, which is a major nerve landmark, may be selected as the anatomical structure of interest. However, this is merely an example, and a method of selecting the reference anatomical structure or the anatomical structure of interest is not limited to the above-described embodiment.

Meanwhile, when an ultrasonic image, which is certain volume data acquired based on consecutive 2-dimensional cross sections, is acquired, an anatomical structure of interest may need to be identified for each ultrasonic image frame showing each 2-dimensional cross section.

For example, when an ultrasonic image is acquired in a direction from a distal wrist to a proximal wrist of a user, an ulnar nerve, which is an anatomical structure of interest, may need to be consecutively identified in each frame. In an embodiment, an ultrasound diagnosis apparatus may acquire an anatomical structure of interest or an estimated position thereof for each frame constituting volume data in the manner described with reference to FIGS. 3 and 4. In addition, the ultrasound diagnosis apparatus may use an anatomical structure of interest or an estimated position thereof acquired in a previous frame to acquire an anatomical structure of interest or an estimated position thereof in a current frame. For example, the ultrasound diagnosis apparatus may select an anatomical structure of interest or an estimated position thereof acquired in a previous frame as an additional reference point in a current frame. The ultrasound diagnosis apparatus may display an anatomical structure of interest or an estimated position thereof acquired in a previous frame and may display a relationship with an anatomical structure of interest or an estimated position thereof acquired in a current frame. For example, the ultrasound diagnosis apparatus may display the relationship in the form of a natural language description of "branch nerve separated to left side from nerve of previous frame."

FIGS. 7A to 7D are images for describing methods of displaying an anatomical structure of interest and information about the anatomical structure of interest according to an embodiment.

Figure 7A:
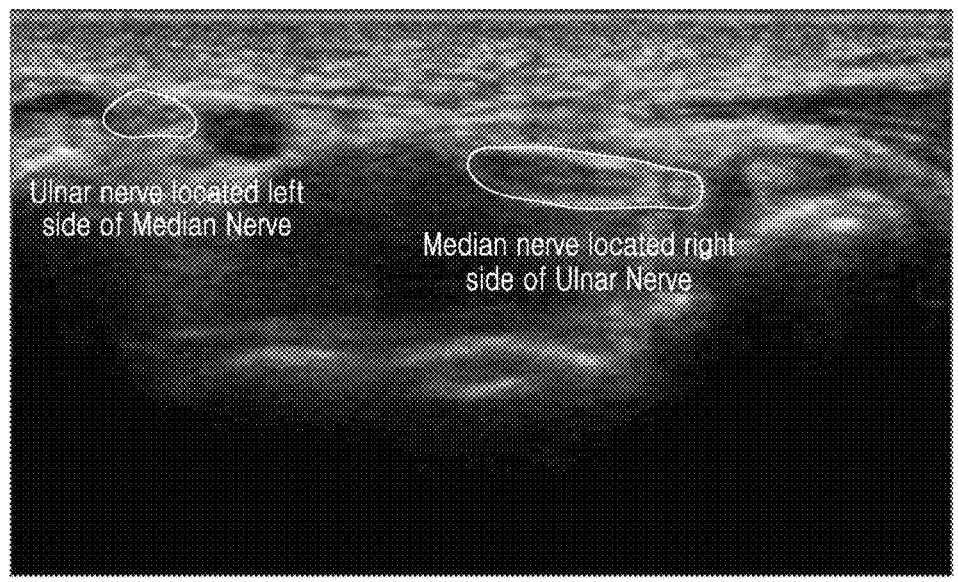
FIG. 7A is an image for describing a method of displaying an anatomical structure of interest and information about the anatomical structure of interest according to an embodiment.

Specifically, FIG. 7A is an image showing an embodiment in which an anatomical structure of interest is displayed in the form of a closed curve, and information about the anatomical structure of interest is displayed in the form of a natural language description. Referring to FIG. 7A, a position of an ulnar nerve as an exemplary reference anatomical structure and a position of a median nerve as an exemplary anatomical structure of interest are displayed in the form of a closed curve, and information indicating a positional relationship between the anatomical structure of interest and a reference point is displayed in the forms of "ulnar nerve located on left side of median nerve" and "median nerve located on right side of ulnar nerve."

Figure 7B:
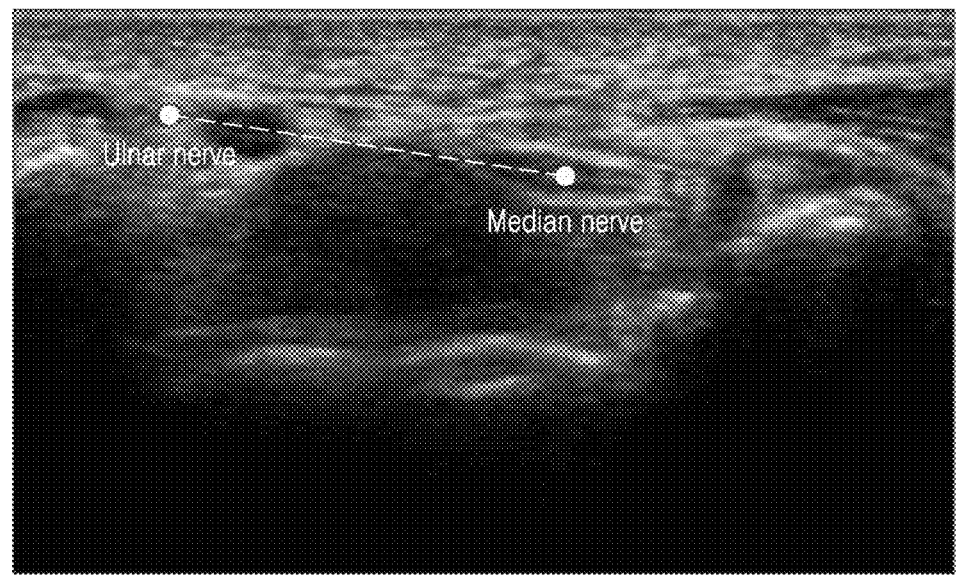
FIG. 7B is an image for describing a method of displaying an anatomical structure of interest and information about the anatomical structure of interest according to an embodiment.

FIG. 7B is an image showing an embodiment in which an anatomical structure of interest is displayed in the form of a dot as an identifier and the form of text of a name, and information about the anatomical structure of interest is displayed in the form of a distance map. Referring to FIG. 7B, a position of an ulnar nerve as an exemplary reference anatomical structure and a position of a median nerve as an exemplary anatomical structure of interest are displayed in the form of a dot and the form of text of a name, and information indicating a positional relationship between the anatomical structure and a reference point is displayed in the form of information indicating a distance d between the anatomical structure of interest and the reference point and the form of a line connecting the anatomical structure of interest and the reference point.

Figure 7C:
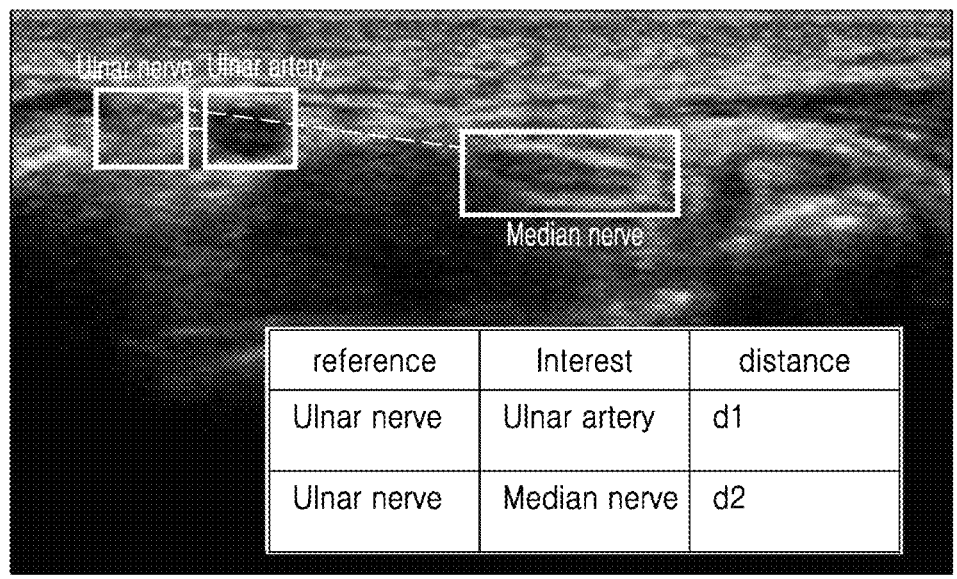
FIG. 7C is an image for describing a method of displaying an anatomical structure of interest and information about the anatomical structure of interest according to an embodiment.

FIG. 7C is an image showing an embodiment in which an anatomical structure of interest is displayed in the form of a box and the form of text of a name, and information about the anatomical structure of interest is displayed in the form of a distance table. Referring to FIG. 7C, a position of an ulnar nerve as an exemplary reference anatomical structure and positions of a median nerve and an ulnar artery as exemplary anatomical structures of interest are displayed in the form of a box and the form of text of a name, and pieces of information indicating positional relationships between the anatomical structures of interest and a reference point are displayed in the form of a table showing distances d1 and d2 between the anatomical structures of interest and the reference point and the form of lines connecting the anatomical structures of interest and the reference point.

Figure 7D:
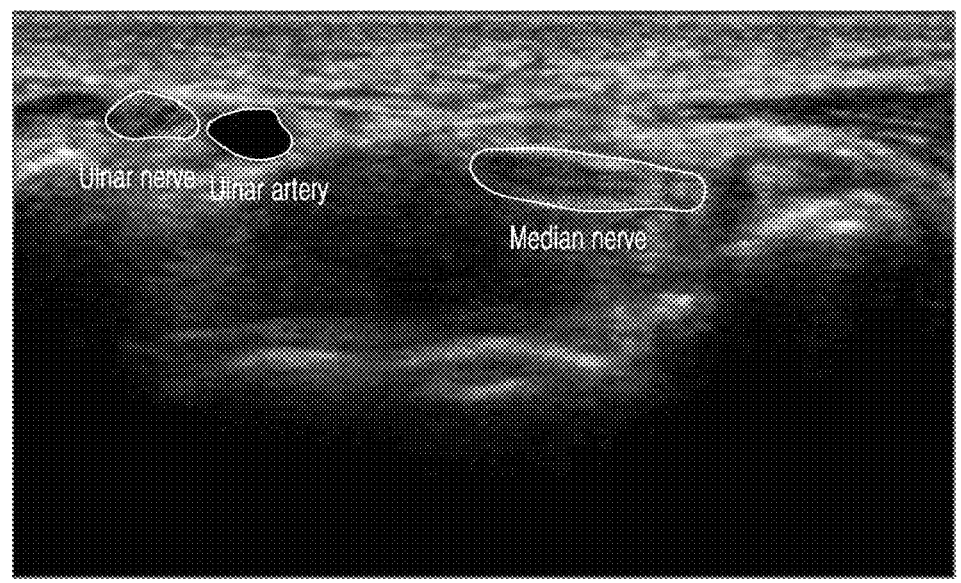
FIG. 7D is an image for describing a method of displaying an anatomical structure of interest and information about the anatomical structure of interest according to an embodiment.

FIG. 7D is an image showing an embodiment in which an anatomical structure of interest is displayed in the form of a face and the form of text of a name, and information about of the anatomical structure of interest is displayed in the form of a distance color map. Referring to FIG. 7D, a position of an ulnar nerve as an exemplary reference anatomical structure and positions of a median nerve and an ulnar artery as exemplary anatomical structures of interest are displayed in the form of a face and the form of text of a name, and pieces of information indicating positional relationships between the anatomical structures of interest and a reference point are displayed in the form of a face of which a color is varied according to a distance between the anatomical structures of interest and the reference point. For example, in FIG. 7D, since a distance between the ulnar nerve and the median nerve is longer than a distance between the ulnar nerve and the ulnar artery, the color of the face indicating the median nerve is displayed brighter than the color of the face indicating the ulnar artery.

FIGS. 8A to 8D are images for describing methods of displaying an estimated position of an anatomical structure of interest and a probability of the estimated position according to an embodiment.

Figure 8A:
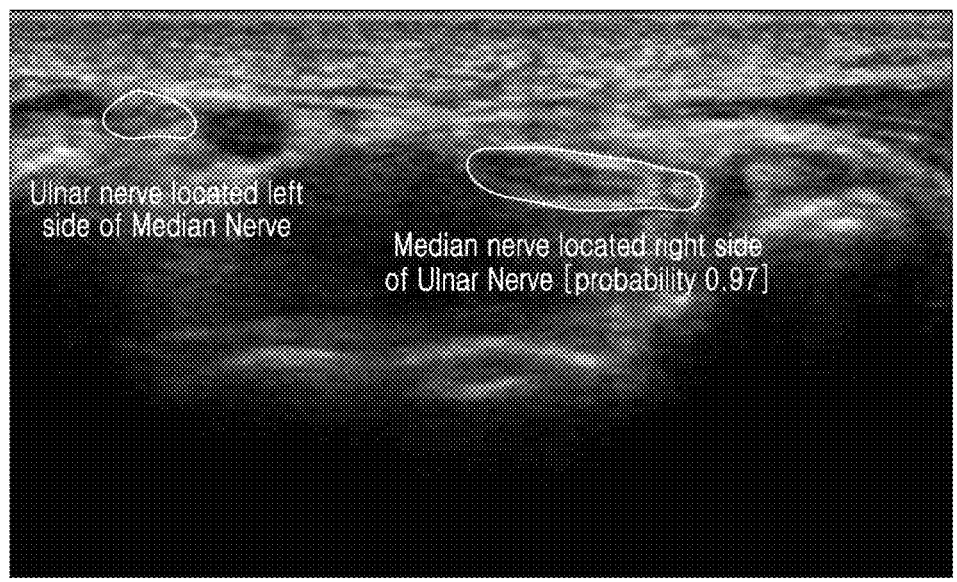
FIG. 8A is an image for describing an estimated position of an anatomical structure of interest and a probability of the estimated position according to an embodiment.

Specifically, FIG. 8A is an image showing an embodiment in which an estimated position of an anatomical structure of interest is displayed in the form of a closed curve, and information about the anatomical structure of interest and a probability are displayed in the form of a natural language description. Referring to FIG. 8A, a position of an ulnar nerve as an exemplary reference anatomical structure and a position of a median nerve as an exemplary anatomical structure of interest are displayed in the form of a closed curve, and information indicating a positional relationship between the anatomical structure of interest and a reference point, and a probability are displayed in the form of "ulnar nerve located on left side of median nerve" and "median nerve located on right side of ulnar nerve [probability 0.97]."

Figure 8B:
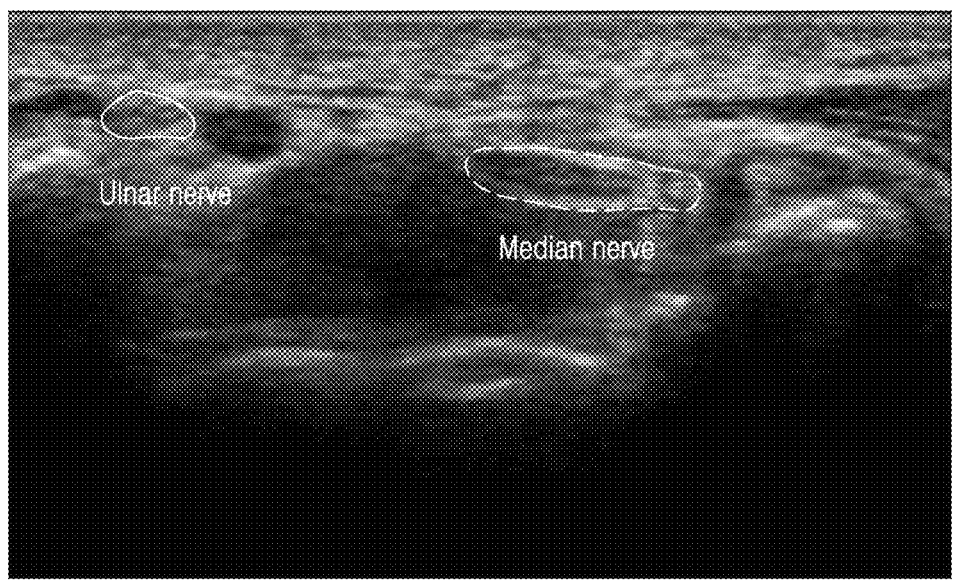
FIG. 8B is an image for describing an estimated position of an anatomical structure of interest and a probability of the estimated position according to an embodiment.

FIG. 8B is an image showing an embodiment in which an anatomical structure of interest is displayed in the form of a closed curve and the form of text of a name, and a probability is displayed as a type of line. Referring to FIG. 8B, a position of an ulnar nerve as an exemplary reference anatomical structure and a position of a median nerve as an exemplary anatomical structure of interest are displayed in the form of a closed curve and the form of text of a name, and when a probability is less than or equal to a certain value, the above-described closed curve is displayed in the form of a dotted line.

Figure 8C:
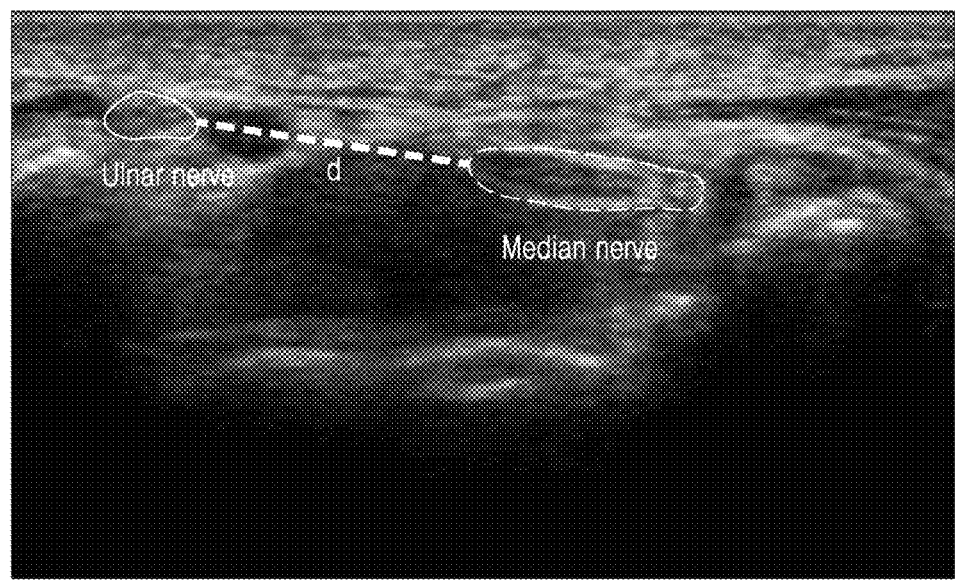
FIG. 8C is an image for describing an estimated position of an anatomical structure of interest and a probability of the estimated position according to an embodiment.

FIG. 8C is an image showing an embodiment in which an anatomical structure of interest is displayed in the form of a closed curve and the form of text of a name, information about the anatomical structure of interest is displayed in a distance map, and a probability is displayed as a type of line. Referring to FIG. 8C, a position of an ulnar nerve as an exemplary reference anatomical structure and a position of a median nerve as an exemplary anatomical structure of interest are displayed in the form of a closed curve and the form of text of a name, information indicating a positional relationship between the anatomical structure and a reference point is displayed in the form of information indicating a distance d between the anatomical structure of interest and the reference point and the form of a line connecting the anatomical structure of interest and the reference point, and when a probability is less than or equal to a certain value, the above-described closed curve is displayed in the form of a dotted line.

Figure 8D:
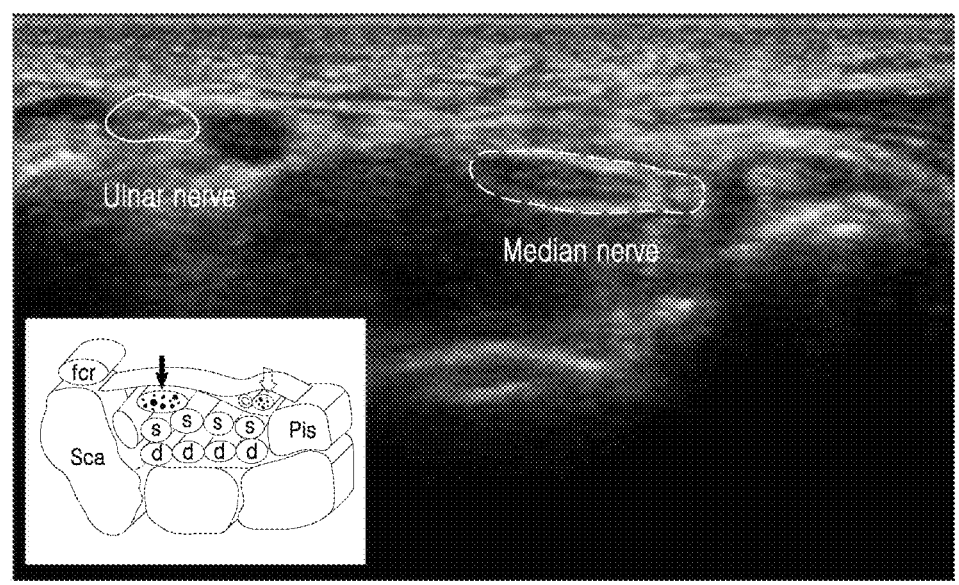
FIG. 8D is an image for describing an estimated position of an anatomical structure of interest and a probability of the estimated position according to an embodiment.

FIG. 8D is an image showing an embodiment in which an anatomy corresponding to a reference anatomical structure or an anatomical structure of interest is additionally displayed in the embodiment of FIG. 8A. Referring to FIG. 8D, an image in which a position of an ulnar nerve as an exemplary reference anatomical structure and a position of a median nerve as an exemplary anatomical structure of interest are displayed in the form of a closed curve, information indicating a positional relationship between the anatomical structure of interest and a reference point, and a probability are displayed in the form of "ulnar nerve located on left side of median nerve" and "median nerve located on right side of ulnar nerve [probability 0.97]," and an image is displayed which shows the position of the ulnar nerve as the reference anatomical structure and a structure of the median nerve as the exemplary anatomical structure of interest.

Figure 9:
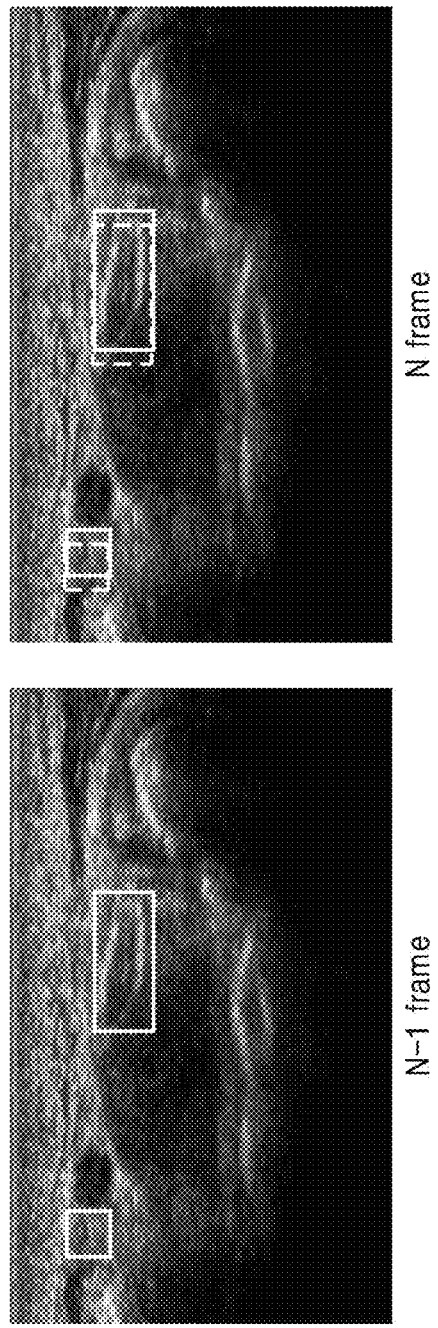
FIG. 9 shows images for describing an ultrasonic image display method according to an embodiment.

FIG. 9 shows images for describing an ultrasonic image display method according to an embodiment.

When an ultrasonic image, which is certain volume data acquired based on consecutive 2-dimensional cross sections, is acquired, an anatomical structure of interest may need to be identified for each ultrasonic image frame showing each 2-dimensional cross section.

In an embodiment, an ultrasound diagnosis apparatus may acquire an anatomical structure of interest or an estimated position thereof for each frame constituting volume data in the manner described with reference to FIGS. 3 and 4. In addition, the ultrasound diagnosis apparatus may use an anatomical structure of interest or an estimated position thereof acquired in a previous frame to acquire an anatomical structure of interest or an estimated position thereof in a current frame.

Referring to FIG. 9, for example, an ulnar nerve and a median nerve as anatomical structures of interest in a current frame are displayed in the form of a box. More specifically, in an N frame, positions of the ulnar nerve and the median nerve as the anatomical structures of interest are shown together with positions of an ulnar nerve and a median nerve of an N−1 frame, which are displayed in the form of a dotted line and are reference points in the N frame.

Meanwhile, the disclosed embodiments may be implemented through recording media having stored therein computer-executable instructions. The instructions may be stored in the form of program codes, and when executed by processor, generate a program module to perform operations of the disclosed embodiments. Furthermore, when being executed by the processor, the instructions may perform certain operations of the disclosed embodiments.

The invention claimed is:

1. An ultrasonic 2-dimensional (2D) image display method comprising:
    acquiring the ultrasonic 2D image including a proximal carpal tunnel, wherein the ultrasonic 2D image shows a cross section of the proximal carpal tunnel;
    determining a reference point in the ultrasonic 2D image, wherein one of a plurality of landmark anatomical structures included in the proximal carpal tunnel is selected as the reference point;
    identifying at least one anatomical structures of interest based on a positional relationship with the reference point on the basis of the determined reference point, wherein the at least one anatomical structures of interest is identified from among the plurality of landmark anatomical structures except the reference point, and the positional relationship includes a 2-dimensional distance value in the ultrasonic 2D image, a direction in the ultrasonic 2D image, and a natural language description indicating the 2-dimensional distance value and the direction between the anatomical structure of interest and the reference point; and
    displaying the identified anatomical structure of interest of the proximal carpal tunnel and information about the anatomical structure of interest on the ultrasonic image or parallel with the ultrasonic 2D image,
    wherein the information about the anatomical structure of interest is information indicating the positional relationship between the anatomical structure of interest and the reference point.

2. The ultrasonic image display method of claim 1, wherein the identifying of at least one anatomical structures of interest based on the positional relationship with the reference point on the basis of the determined reference point further includes identifying the anatomical structure of interest on the ultrasonic image by applying data about the reference point and the anatomical structure of interest to a learning model, and
    learning model is trained through position context information.

3. The ultrasonic image display method of claim 1, wherein the anatomical structure of interest is determined based on an input of a user selecting a specific anatomical structure from among a plurality of anatomical structures.

4. The ultrasonic image display method of claim 1, wherein the plurality of landmark anatomical structures of the proximal carpal tunnel includes at least one of an ulnar artery, an ulnar nerve, a median nerve, a scaphoid tubercle, a pisiform, a flexor retinaculum, and a flexor pollicis longus.

5. The ultrasonic image display method of claim 1, wherein the reference point is determined based on an input of a user.

6. The ultrasonic image display method of claim 5, wherein the reference point is determined based on a click event of the user at a specific position in the ultrasonic image or an input of the user related to position coordinates.

7. The ultrasonic image display method of claim 1, wherein the reference point is determined based on a point at which at least one reference anatomical structure is located on the ultrasonic image.

8. The ultrasonic image display method of claim 7, wherein the at least one reference anatomical structure is determined based on an input of a user selecting a specific anatomical structure from among a plurality of anatomical structures.

9. The ultrasonic image display method of claim 1, wherein the identifying of at least one anatomical structures of interest based on the positional relationship with the reference point on the basis of the determined reference point further includes:
    determining whether the at least one anatomical structures of interest are identifiable; and
    when it is determined that the at least one anatomical structures of interest are unidentifiable, acquiring an estimated position of the at least one anatomical structures of interest on the ultrasonic image based on the positional relationship on the basis of the reference point.

10. The ultrasonic image display method of claim 9, further comprising:
    calculating a probability of the estimated position; and
    displaying the calculated probability.

11. An ultrasonic imaging apparatus comprising:
    a display unit;
    a user interface;
    a memory configured to store one or more instructions, and
    a processor configured to:
    acquire an ultrasonic 2-dimensional (2D) image including a proximal carpal tunnel, wherein the ultrasonic 2D image shows a cross section of the proximal carpal tunnel;
    determine a reference point in the ultrasonic 2D image, wherein one of a plurality of landmark anatomical structures included in the proximal carpal tunnel is selected as the reference point,
    identify at least one anatomical structure of interest based on a positional relationship with the reference point on the basis of the determined reference point, wherein the at least one anatomical structures of interest is identified from among the plurality of landmark anatomical structures except the reference point, and the positional relationship includes a 2-dimensional distance value in the ultrasonic 2D image, a direction in the ultrasonic 2D image, and a natural language description indicating the 2-dimensional distance value and the direction between the anatomical structure of interest and the reference point, and
    control the display unit to display the identified anatomical structure of interest of the proximal carpal tunnel and information about the anatomical structure of interest on the ultrasonic image or parallel with the 2D ultrasonic image,
    wherein the information about the anatomical structure of interest is information indicating the positional relationship between the anatomical structure of interest and the reference point.

12. The ultrasonic imaging apparatus of claim 11, wherein the reference point is determined based on a point at which at least one reference anatomical structure is located on the ultrasonic image.

13. The ultrasonic imaging apparatus of claim 11, wherein the processor identifies the anatomical structure of interest on the ultrasonic image by applying data about the reference point and the anatomical structure of interest to a learning model, and the learning model is trained through position context information.

14. The ultrasonic imaging apparatus of claim 11, wherein it is determined whether the at least one anatomical structure of interest is identifiable, and
    when it is determined that the at least one anatomical structure of interest is unidentifiable, an estimated position of the at least one anatomical structure of interest on the ultrasonic image is acquired based on the positional relationship on the basis of the reference point.

15. The ultrasonic imaging apparatus of claim 11, wherein the plurality of landmark anatomical structures of the proximal carpal tunnel includes at least one of an ulnar artery, an ulnar nerve, a median nerve, a scaphoid tubercle, a pisiform, a flexor retinaculum, and a flexor pollicis longus.

16. A non-transitory computer-readable recording medium for storing a computer program code for, when being read and executed by a processor, performing an ultrasonic 2-dimensional (2D) image display method, wherein the ultrasonic 2D image display method includes:
    acquiring the ultrasonic 2D image including a proximal carpal tunnel, wherein the ultrasonic 2D image shows a cross section of the proximal carpal tunnel;
    determining a reference point in the ultrasonic 2D image, wherein one of a plurality of landmark anatomical structures included in the proximal carpal tunnel is selected as the reference point;
    identifying at least one anatomical structure of interest based on a positional relationship with the reference point on the basis of the determined reference point, wherein the at least one anatomical structures of interest is identified from among the plurality of landmark anatomical structures except the reference point, and the positional relationship includes a 2-dimensional distance value in the ultrasonic 2D image, a direction in the ultrasonic 2D image, and a natural language description indicating the 2-dimensional distance value and the direction between the anatomical structure of interest and the reference point;
    displaying the identified anatomical structure of interest of the proximal carpal tunnel and information about the anatomical structure of interest on the ultrasonic 2D image or parallel with the ultrasonic image,
    wherein the information about the anatomical structure of interest is information indicating the positional relationship between the anatomical structure of interest and the reference point.

17. The non-transitory computer-readable recording medium of claim 16, wherein the plurality of landmark anatomical structures of the proximal carpal tunnel includes at least one of an ulnar artery, an ulnar nerve, a median nerve, a scaphoid tubercle, a pisiform, a flexor retinaculum, and a flexor pollicis longus.

* * * * *